(12) United States Patent
Kawase et al.

(10) Patent No.: US 6,922,639 B2
(45) Date of Patent: Jul. 26, 2005

(54) GAS CONCENTRATION DETECTING APPARATUS

(75) Inventors: Tomoo Kawase, Aichi-ken (JP); Eiichi Kurokawa, Okazaki (JP)

(73) Assignee: Denso Corporation, Kariya (JP)

( * ) Notice: Subject to any disclaimer, the term of this patent is extended or adjusted under 35 U.S.C. 154(b) by 112 days.

(21) Appl. No.: 10/678,095

(22) Filed: Oct. 6, 2003

(65) Prior Publication Data

US 2004/0138825 A1 Jul. 15, 2004

(30) Foreign Application Priority Data

Oct. 10, 2002 (JP) ........................................ 2002-297773

(51) Int. Cl.[7] .............................................. G06F 19/00
(52) U.S. Cl. .......................... 702/24; 702/22; 204/424; 204/425; 205/781; 73/23.31
(58) Field of Search .................... 702/24, 22, 30; 204/424, 425, 426, 427, 406, 408; 205/781, 783, 783.5, 785; 73/23.31, 23.32, 31.05, 35.05

(56) References Cited

U.S. PATENT DOCUMENTS

| | | |
|---|---|---|
| 5,810,997 A | 9/1998 | Okazaki et al. |
| 6,231,735 B1 * | 5/2001 | Poggio et al. ............... 204/425 |
| 6,295,862 B1 * | 10/2001 | Kurokawa et al. .......... 73/31.05 |
| 6,656,337 B2 * | 12/2003 | Kurokawa et al. ........... 204/425 |
| 6,695,964 B1 * | 2/2004 | Ando et al. .................. 205/781 |

FOREIGN PATENT DOCUMENTS

| | | |
|---|---|---|
| JP | 9-61397 | 3/1997 |
| JP | 2002-202285 | 7/2002 |

* cited by examiner

*Primary Examiner*—Bryan Bui
*Assistant Examiner*—Hien Vo
(74) *Attorney, Agent, or Firm*—Nixon & Vanderhye P.C.

(57) ABSTRACT

A gas concentration detecting apparatus comprises a gas concentration sensor and a gas concentration calculator. The sensor has first to third cells. A gas to be detected is introduced in a chamber and the first cell is responsible for discharging and changing oxygen from and into the chamber. The second cell detects a concentration of a specific gas component of the gas that has passed along the first cell. The third cell detects a concentration of residual oxygen in the gas that remains after discharge of the oxygen through the first cell. The calculator takes in a current acquired from the second cell measured with a voltage applied thereto and calculates the specific gas component concentration based on the current. The calculator includes plural concentration calculating means whose concentration detecting ranges are mutually different in a scale. The specific gas component concentration is calculated every concentration calculating means.

20 Claims, 11 Drawing Sheets

[PUMP CELL CURRENT (mA)]

| OXYGEN CONCENTRATION | | |
|---|---|---|
| 0% | 10% | 20% |
| 0 | 1.25 | 2.50 |

FIG. 8A

[NOx-DETECTING CURRENT (nA)]

| NOx CONCENTRATION | OXYGEN CONCENTRATION | | |
|---|---|---|---|
| | 0% | 10% | 20% |
| 0ppm | 60 | 63 | 66 |
| 100ppm | 375.46 | 406.6 | 443.3 |
| 300ppm | 996.58 | 1084.6 | 1184.0 |

FIG. 8B

[CORRECTION DATA]

| | | OXYGEN CONCENTRATION | | |
|---|---|---|---|---|
| | | 0% | 10% | 20% |
| PUMP CELL CURRENT (mA) | | 0 | 1.25 | 2.50 |
| CORRECTING VALUE FOR ZERO-POINT SHIFT (nA) | | 60 | 63 | 66 |
| RANGE-DETERMINING VALUE (nA) | | 375.46 | 406.6 | 443.3 |
| SENSITIVITY-CORRECTING COEFFICIENT (ppm/nA) | 0-100ppm RANGE | 0.317 | 0.291 | 0.265 |
| | 100-300ppm RANGE | 0.322 | 0.295 | 0.270 |

FIG. 8C

GAS CONCENTRATION DETECTING APPARATUS

BACKGROUND OF THE INVENTION

1. The Field of the Invention

The present invention relates to an apparatus for detecting a concentration of a gas

2. Related Art

A gas concentration detecting apparatus has many types depending on applications. One type, as disclosed by Japanese Patent Laid-open (KOKAI) publication No. 2002-20285, is an apparatus that employs a limiting current type of gas concentration sensor in order to, for example, detect NOx (nitrogen oxide) included in an exhaust gas discharged from an automobile engine. In this apparatus, the gas concentration sensor is structured, as an example, to have three cells consisting of a pump cell, a sensor cell, and a monitor cell. The pump cell is responsible for discharging and drawing oxygen in an exhaust gas taken into a chamber, during which time the pump cell detects an oxygen concentration in the exhaust gas. The sensor cell detects a NOx concentration (i.e., a concentration of a particular gas component) from the gas that has passed the pump cell, and the monitor cell detects a concentration of oxygen that is residual in the chamber after the gas has passed the pump cell.

In detail, the detection of the NOx concentration can be performed such that a censor cell current is measured in response to application of voltage to the sensor cell, and a signal indicative of the measured current is fed to a microcomputer via an A/D converter. The microcomputer converts the digitized current signal to a corresponding concentration, resulting in acquisition of the value of the NOx concentration.

For using the gas concentration sensor as an exhaust gas sensor, a signal indicating the value of the NOx concentration is, for example, outputted to an engine ECU controlling the engine. The engine ECU uses the signal to control the engine for the purpose of absorbed NOx is deoxidized and discharged with the use of a NOx occlusion-deoxidization type catalyst and uses the signal as information indicative of failure diagnosis of sensors or others under the regulations such as OBD. In such a case where the regulations such as OBD is effective, it is necessary to detect a NOx concentration in a concentration detecting range whose range is wider than that used for the normal control. Thus, the detection range for the NOx concentration and others are previously determined in accordance with the regulations.

However, as described above, in cases where the NOx concentration should be given to plural applications and the regulatory compliance forces the concentration detecting range to be extended, resolution for the NOx concentration becomes rough, because a microcomputer or other processing apparatuses are usually limited in a processing facility. When such applications are directed to the regulations such as OBD, any problem will not arise even if the resolution for the NOx concentration is relatively rough. In contrast, for applications such as engine control, such a limited processing capability may cause a problem that a desired concentration detecting accuracy cannot be met. Recently, there is a tendency that the regulations for emission of the exhaust gas have been strengthened increasingly. It is therefore desired to overcome these situations.

SUMMARY OF THE INVENTION

An object of the present invention is to provide, with due consideration to the above-said situations, a gas concentration detecting apparatus capable of detecting a gas concentration at a desired detection accuracy for any application, in the case that it is necessary that information indicative of the detected gas concentration be given to a plurality of applications.

There is provided a gas concentration detecting apparatus comprising: a gas concentration sensor provided with a first cell for discharging oxygen contained in a gas to be detected introduced in a chamber from the chamber and for charging oxygen into the chamber, a second cell for detecting a concentration of a specific gas component of the gas that has passed along the first cell, and a third cell for detecting a concentration of residual oxygen in the gas that remains after the oxygen has been discharged through the first cell; and a gas concentration calculator configured to take in a current signal acquired from the second cell measured with a voltage applied to at least the second cell and calculate the concentration of the specific gas component based on the current signal acquired from the second cell, the gas concentration calculator including a plurality of concentration calculating means of which concentration detecting ranges are different in a scale from each other and the concentration of the specific gas component being calculated every concentration calculating means.

In the gas concentration calculator, a plurality of concentration calculating means are provided, so that their concentration detecting ranges can be set differently in a scale from each other. Resolution for the concentration in each of the concentration calculating means can therefore be set individually. Compared to the concentration calculating means having a larger concentration detecting range, the concentration calculating means having a larger concentration detecting range shows a smaller concentration resolution. In consequence, precision for detecting the specific gas component can be raised. In any application, it is therefore possible to meet a desired gas detecting precision.

Preferably, the gas concentration calculator is provided with a plurality of controllers to which the concentrations of the specific gas component calculated by the concentration calculating means are supplied, respectively. Thus, information in relation to the concentrations of the specific gas component can be used arbitrarily depending on applications, thus a practical sensor configuration can be given.

Still preferably, the gas concentration sensor is arranged to an exhaust duct of an engine mounted in a vehicle so that an exhaust gas flowing through the exhaust duct is treated as the gas to be detected and a concentration of a specific gas component of the exhaust gas is detected, wherein, of the plurality of concentration calculating means, concentration calculating means of which concentration detecting range is smaller is assigned to calculation of the concentration of the specific gas component for controlling the engine and further concentration calculating means of which concentration detecting range is larger is assigned to calculation of the concentration of the specific gas component for diagnosing a fault of the engine. Therefore the engine control can be performed with a higher-accuracy concentration of the specific gas component, while the failure diagnosis can be done with a concentration of the specific gas component which is less than the higher-accuracy concentration. The gas concentration sensor according to the present invention is able to detect a NOx concentration and/or a HC concentration in an exhaust gas.

The concentration of the specific gas component is detected from a gas in the second cell, the gas having passed along the first cell. The gas still contains residual oxygen, with the result that the residual oxygen caused an offset error in the second sell current. It is possible to detect this offset error by measuring the third cell current. Thus subtracting the third cell current from the second cell current provides a second cell current of which offset error is removed, improving detection accuracy of the concentration of the specific gas component. It is therefore desired to perform such subtraction to detect the concentration of the specific gas component.

In light of the significance of the above subtraction, the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

In this configuration, before the A/D conversion, the differential amplifying circuit (that is, hardware circuit) operates to remove, through its subtraction, an offset error component (which corresponds to the third cell current signal) from the second cell current signal. Hence the gain given to the differential amplifying circuit can be raised, which widens the dynamic range of a signal to be inputted to the A/D converter. This leads to an increase in the resolution of the A/D conversion, compared to a configuration where the second cell current signal containing an offset error component is directly subjected to the A/D conversion (conventionally, the offset error component obliged the A/D converter to have a wider input range, thus lowering the resolution).

Further, when considering the significance of the foregoing subtraction, it is still preferred that the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, both of the differential amplifying circuit and the A/D converter belonging to, of the plurality of concentration calculating means, concentration calculating means of which concentration detecting range is small, whereby the digitized signal is provided to the computation of the concentration of the specific gas component.

According to this configuration, at least in concentration calculating means of which concentration detecting range is small, the foregoing subtraction can be carried out before the A/D conversion. Therefore, the advantage that the dynamic range of a signal to be inputted the A/D converter is raised can be provided in the similar way to the foregoing. This advantage can accelerate the foregoing improvement in precision of detecting the concentration, when such subtraction configuration is applied to the concentration calculating means of which concentration detecting range is small.

According to the present invention, there is also provided a gas concentration detecting apparatus comprising: a gas concentration sensor provided with a first cell for discharging oxygen contained in a gas to be detected introduced in a chamber from the chamber and for charging oxygen into the chamber, a second cell for detecting a concentration of a specific gas component a gas that has passed along the first cell, and a third cell for detecting a concentration of residual oxygen in the gas that remains after the oxygen has been discharged through the first cell; and a gas concentration calculator is provided with a circuit to take in a current signal acquired from the second cell measured with a voltage applied to the second cell and to take in a current signal acquired from the third cell measured with a voltage applied to the third cell, a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

In this configuration, the foregoing subtraction can also be carried out before the A/D conversion. Therefore, the advantage that the dynamic range of a signal to be inputted the A/D converter is raised can be provided.

On the other hand, current flows through the second cell corresponding to the concentration of a specific gas component in response to voltage application, and the current is measured. In this measurement, the current signal fluctuates in dependence of a concentration of the specific gas component. Moreover, even when the concentration of the specific gas component keeps the same value, the second sell current depends on an oxygen concentration in a gas to be detected. This is because the activation capacity of censor cell electrodes comes short with an increase in a concentration of the specific gas component and/or the oxygen discharging operation of the pump cell is enhanced with an increase in a concentration of oxygen in the gas to be detected, resulting in an excessive charge of the gas into the chamber. Hence it is preferred to perform the following various types of correction.

Preferably, the gas concentration calculator is provided with means for correcting sensitivity in computing the concentration of the specific gas component depending on the current concentration of the specific gas component. Still preferably, the gas concentration calculator is provided with means for correcting an oxygen concentration dependency in computing the concentration of the specific gas component depending on a current concentration of oxygen included in the gas to be detected.

It is preferred that the gas concentration calculator is provided with a memory in which map data is stored, the map data being defined by employing as parameters both of the concentration of the specific gas component included in the gas to be detected and a concentration of oxygen included in gas to be detected, means for setting a sensitivity correction coefficient by using the map data depending on the current concentrations of the specific gas component and the oxygen, and means for correcting the concentration of the specific gas component with the use of the sensitivity correction coefficient.

Accordingly, the foregoing configurations for the correction allow actual characteristics of the sensor to be reflected to its operations for calculating the concentrations based of the measured various current signals, thereby enhancing precision in detecting gas concentrations. Still, the foregoing sensitivity correction and oxygen-concentration-dependency correction can be performed every sensor, so that differences among the sensing characteristics of the sensors can be lessened or eliminated.

BRIEF DESCRIPTION OF THE DRAWINGS

In the accompanying drawings:

FIGS. 8A to 8C explain procedures for setting correction data;

DETAILED DESCRIPTION OF THE PREFERRED EMBODIMENT

An embodiment of the present invention will now be described in conjunction with the appended drawings.

An embodiment of the present invention will now be described in connection with the appended drawings. In this embodiment, a gas concentration detecting apparatus applied to for instance the automobile engine is provided. The apparatus employs a limiting current type of gas concentration sensor to detect not only an oxygen concentration of an exhaust gas serving as a gas to be detected but also a NOx concentration as a concentration of a particular gas component included in the exhaust gas.

Figure 1A:
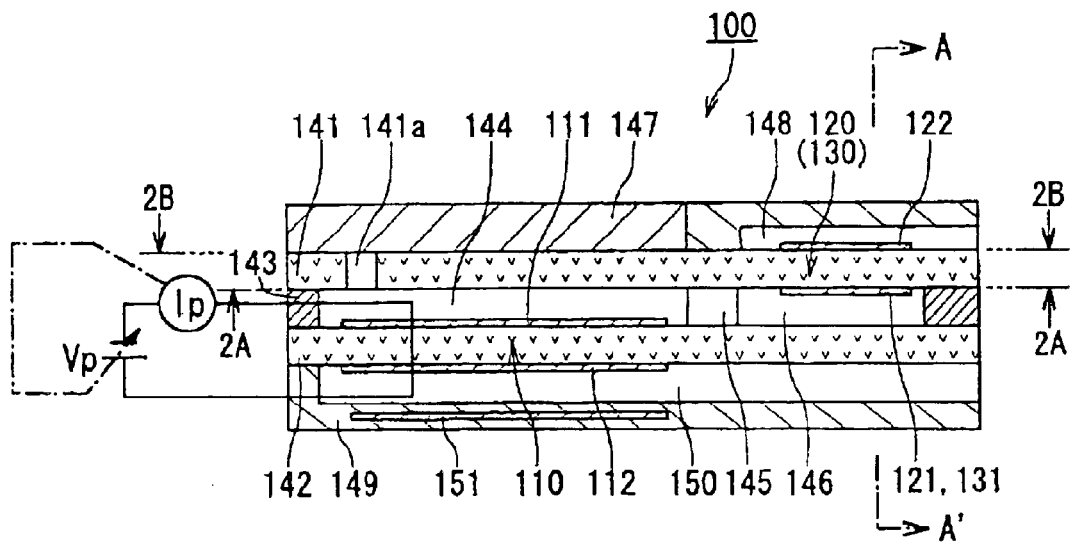
FIG. 1A is a sectional view of a gas concentration sensor according to an embodiment of the present invention.
Figure 1B:
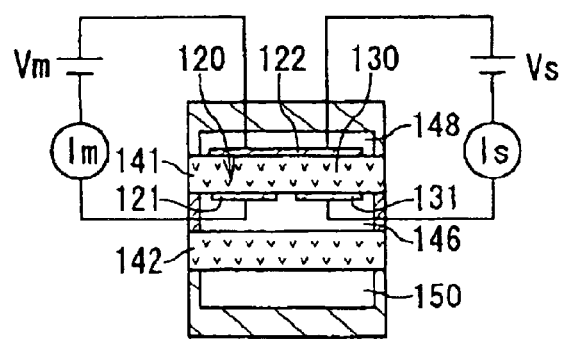
FIG. 1B is another sectional view of the gas concentration sensor according to the embodiment, which is taken along an A—A line in FIG. 1A.

First of all, with reference to FIGS. 1A and 1B, the configuration of a gas concentration sensor 100 will now be described. The gas concentration sensor 100 shown in FIGS. 1A and 1B is structured to have three cells consisting of "a pump cell" serving as "a first cell," "a sensor cell" serving as a "second cell," and "a monitor cell" serving as "a third cell," which is therefore formed into a compound type of gas sensor capable of simultaneously detecting both of an oxygen concentration and a NOx concentration included in an exhaust gas. In some cases, the monitor cell is referred to as a second pump cell, because the monitor cell is functionally similar to the pump cell in that the monitor cell has the function of discharging the oxygen of the gas from the chamber. FIG. 1A shows a sectional structure of the tip of the sensor 100, while FIG. 1B is a section showing cut along an A—A line in FIG. 1A.

The gas concentration sensor 100 has sheet-like solid electrolytes (solid electrolyte layers) 141 and 142 both formed from an oxygen-ion conductive material and a spacer 143 formed from an insulating material such as alumina. The spacer 143 is placed to allow the solid electrolyte layers 141 and 142 to be located separately from each other predetermined intervals, as shown in FIG. 1A. In FIG. 1A, of the two solid electrolyte layers 141 and 142, one layer 141 located at an upper position has a pin hole 141a formed therethrough. This pin hole 141a allows an exhaust gas around the sensor 100 to be pass therethrough so that the gas flows into a first chamber 144 formed between the solid electrolyte plates 141 and 142. The first chamber 144 communicates with a second chamber 146 via a diaphragm 145. A reference 147 in FIG. 1A shows a porous diffusion layer.

Along the other solid electrolyte layer 142 located on the downside in FIG. 1A, a pump cell 110 is formed to face the first chamber 144. The pump cell 110 is configured to discharge and charge oxygen from and into an exhaust gas that has been introduced into the first chamber 144, during which discharge or charge of the oxygen the pump cell 110 operates to detect a concentration of oxygen contained in the exhaust gas. The pump cell 110 is provided with a pair of upper and lower electrodes 111 and 112 located on both the sides of the solid electrode layer 142. Of these electrodes 111 and 112, the electrode 111 located to be in the first chamber 144 is particularly formed as a NOx-inert electrode (i.e., electrode that is easy to dissolve into the NOx gas). The pump cell 110 is placed to dissolve the oxygen residing in the first chamber 144 and to discharge the dissolved oxygen into an atmosphere-communicating passage 150 via the electrode 112.

In addition, along the solid electrolyte layer 141, a monitor cell 120 and a sensor cell 130 are arranged to face the second chamber 146 formed between the solid electrolyte layers 141 and 142. The monitor cell 120 is responsible for generating an electromotive force depending on a concentration of residual oxygen in the second chamber 146 or a current output in response to application of voltage thereto. Meanwhile the sensor cell 130 is responsible for detecting a concentration of NOx contained of the exhaust gas that passed along the pump cell 110.

Particularly, as shown in FIG. 1B, the present embodiment has a layout where both the monitor cell 120 and the sensor cell 130 are arranged in parallel with each other in the flowing direction of the exhaust gas, so that both cells are subjected to a flow of the gas equally to each other. A common electrode 122 used in common to both the cells 120 and 130 is placed on the layer 141 so as to be in an atmosphere-communicating passage 148. Thus, the monitor cell 120 is composed of the solid electrolyte layer 141 and the two electrodes 121 and 122 placed on both the sides of the layer 141 to be opposed to each other with the layer 141 therebetween. In a similar manner to the monitor cell 120, the sensor cell 130 is composed of the solid electrolyte layer 141 and the two electrodes 131 and 122 placed on both the sides of the layer 141 to be opposed to each other with the layer 141 therebetween.

There is, however, a difference between both the cells 120 and 130. The electrode 121 of the monitor cell 120, which is located to be in the second chamber 146, is made from a noble metal such as Au—Pt which is inert to a NOx gas, while the electrode 131 of the censor cell 130, which is located to be in the second chamber 146, is made from a noble metal such as platinum Pt or rhodium Rh which is active to the NOx.

Figure 2A:
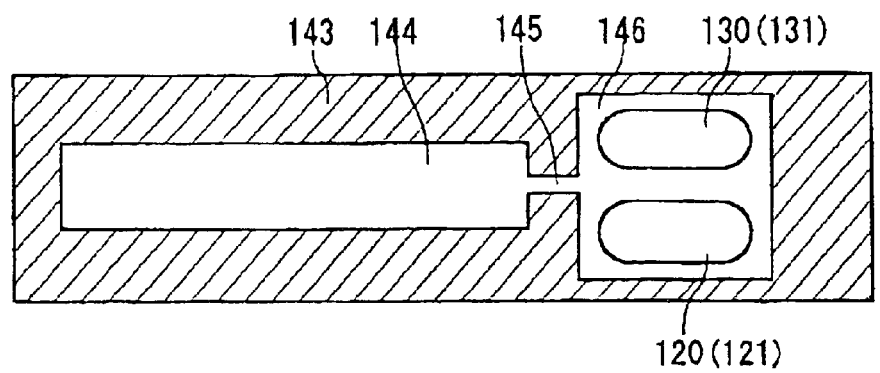
FIGS. 2A and 2B are sectional views explaining the arrangement of electrodes of a monitor cell and a sensor cell embedded in the gas concentration sensor according to the embodiment, which are taken along a 2A—2A line and a 2B—2B line in FIG. 1A, respectively.
Figure 2B:
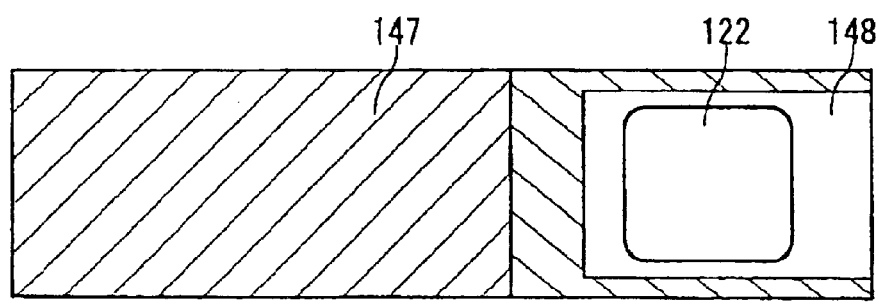

FIG. 2A is a section (taken along a 2A—2A line in FIG. 1A) obtained when viewing the electrodes of both the monitor cell 120 and the sensor cell 130 from the second chamber 146, while FIG. 2B is a section (taken along a 2B—2B line in FIG. 1A) obtained when viewing the electrodes of the cells 120 and 130 from the atmosphere-communicating passage 148. As understood from those sections, both of the monitor cell 120 and the sensor cell 130 are configured to have the same exhaust-gas-introduction distance. As a result, detection sensitivity to the residual oxygen coming along the pump cell 110 is made equal to each other between the monitor cell 120 and the sensor cell 130, leading to higher-accuracy detection of gas concentrations.

The layout of the electrodes of both the cells 120 and 130 is not always confined to the parallel arrangement, as shown in FIG. 2A, in the exhaust-gas flow direction. Alternatively, it is possible to arrange the cells 120 and 130 at two different positions in the exhaust-gas flow direction (i.e., predetermined rightward and leftward positions in FIG. 2A). For instance, the monitor cell 120 is located at an upstream-side position (a leftward position in FIG. 2A) and the sensor cell 130 is located at a downstream position (a rightward position in FIG. 2B). As a further modification, the single common electrode 122 may be replaced by two electrodes respectively used to both the cells 120 and 130.

As shown in FIGS. 1A and 1B, an insulating layer 149, which is made of alumina or others, is placed on the other side of the solid electrolyte layer 142, so that the foregoing atmosphere-communicating passage 150 is formed between the layers 149 and 142. In the insulating layer 149, a heater 151 is embedded to heat the sensor 100 entirely. The heater 151 generates thermal energy in response to power supplied from outside the sensor 100, whereby the entire sensor 100, which includes the pump cell 110, monitor cell 120 and sensor cell 130, becomes active.

The gas concentration sensor 100 configured as above operates as follows.

An exhaust gas is introduced into the first chamber 144 through the porous diffusion layer 147 and the pin hole 141a. Since a voltage Vp is applied to the both the electrodes 111 and 112 of the pump cell 110, a dissolution reaction will occur in the exhaust gas when the gas passes along the pump cell 110. Thus, depending on a concentration of the oxygen in the first chamber 144, the oxygen is taken in and taken out by the pump cell 110. Since the electrode 111, which is located on the first chamber side, is an electrode which is inert to the NOx component, the NOx contained in the exhaust gas will not be subjected to the dissolution caused by the pump cell 110. This means that only the oxygen is subjected to the dissolution, before being discharged into the atmosphere-communicating passage 150. A current flowing through the pump cell 110 (called "pump cell current Ip") is measured to detect a concentration of the oxygen contained in the exhaust gas.

The exhaust gas that has passed along the pump cell 110 and is made to flow into the second chamber 146, thus causing the monitor cell 120 to generate its output in accordance with the concentration of the residual oxygen in the exhaust gas in the second chamber 146. Applying a predetermined amplitude of voltage Vm to both the electrodes 121 and 122 of the monitor cell 120 makes it possible that the output of the monitor cell 120 is detected as a monitor cell current Im. Also, applying a predetermined amplitude of voltage Vs to the electrodes 131 and 122 of the sensor cell 130 causes a NOx component of the exhaust gas to undergo reduction dissolution, thus generating oxygen. This oxygen is discharged into the atmosphere-communicating passage 148. In this case, a current flowing through the sensor cell 130 (called "sensor cell current Is") is measured to detect the concentration of the NOx that the exhaust gas contains.

Incidentally, the pump cell 110 is controlled such that the voltage applied to the pump cell 110 is changed whenever the oxygen concentration of the exhaust gas (i.e., the pump cell current Ip) is changed. By way of example, an application voltage map is made based on the limiting current characteristic of the pump cell 110 and the map is used to control the application voltage Vp according to the current pump cell current Ip. Thus, the application voltage is controlled in such a manner that the higher the oxygen concentration of the exhaust gas, the higher the application voltage.

How to apply the voltage Vp to the pump cell 110 is not necessarily limited to the above manner. For example, the application voltage Vp may be controlled in a feed back manner so that a concentration of residual oxygen in the second chamber 146 becomes constant (that is, the monitor cell current Im becomes constant).

The foregoing control of the application voltage Vp makes it possible that the oxygen of the exhaust gas introduced into the first chamber 144 is discharged quickly, where the concentration of the residual oxygen after expelling the oxygen can be maintained as a desired low-level concentration.

Accordingly, as stated above, after the excessive oxygen included in the exhaust gas is expelled out by the pump cell 110, the gas containing the residual oxygen having a desired low-level concentration is fed to both the monitor cell 120 and the sensor cell 130. Hence the monitor cell 120 is able to measure its monitor cell current Im in which the residual oxygen concentration is reflected, while the sensor cell 130 is able to measure its sensor cell current Is in which the concentration of NOx of the gas is reflected. In this measurement, it is desirable that the sensor cell 130 measure a current value resulting from only the reductional dissolution of the NOx of the gas. Actually, however, the measurement value involves a current component to which the residual oxygen of the gas (a slight amount of oxygen in the gas) contributes. In other words, the measured censor cell current Is includes a current component resulting from a NOx reaction and another current component resulting from a residual oxygen reaction. Of these current components, the current component resulting from a residual oxygen reaction gives rise to an offset error.

To remove this offset error component from the sensor cell current Is, the present embodiment provides the following technique. That is, the measured monitor cell current Im is reduced from the measured sensor cell current Is to obtain the output of a NOx concentration on the basis of a difference "Is−Im." In the following description, for the sake of convenience, the value "Is−Im" is noted as "NOx detection current."

In the following embodiment, the sensor cell current Is provides "a second sell current signal" and the monitor cell current Im provides "a third cell current signal."

Figure 3:
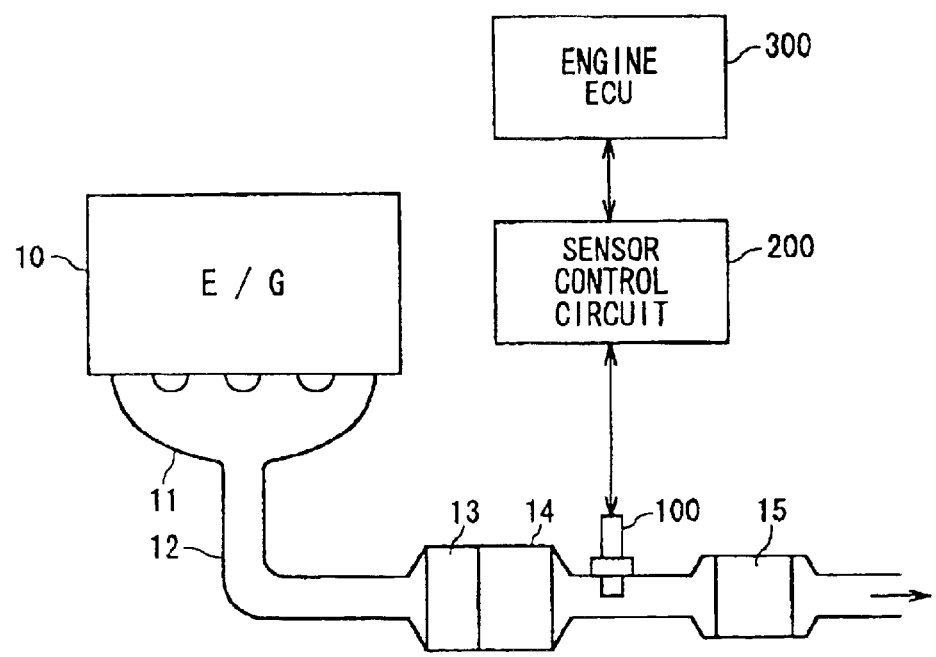
FIG. 3 shows in block form the configuration of an engine exhaust system which employs the gas concentration sensor according to the embodiment.

FIG. 3 shows the configuration of an exhaust system of a diesel engine 10. As shown in FIG. 3, the engine 10 is coupled to an exhaust duct 12 via an exhaust manifold 11. In the exhaust manifold 12, a NOx occlusion-reduction type catalyst 13, DPF (diesel particulate filter) 14, and oxidation catalyst 15 are disposed in this order.

The NOx occlusion-reduction type catalyst 13 is formed to have a catalyst support made of alumina, for example, as has been known. This support is configured to hold, thereon, both of at least one selected from alkali metal including potassium K, natrium Na, lithium Li, and cesium Cs; alkaline earth element including barium Ba and calcium Ca; and rear earth including lanthanum La and yttrium Y, and a noble metal such as platinum Pt. When an air fuel ratio of an exhaust gas is lean, the NOx occlusion-reduction type catalyst 13 absorbs a NOx. In contrast, when the air fuel ratio of the exhaust gas is rich, the sensor 13 discharges the absorbed NOx and deoxidizes the NOx to a nitrogen gas using HC and CO in the exhaust gas. The PDF 14 collects PM (particulates) in the exhaust gas during the passage thereof. The oxidation catalyst 15 causes HC and CO in the exhaust gas to have an oxidative reaction so that $H_2O$ and $CO_2$ are produced, with the exhaust gas discharged.

The foregoing gas concentration sensor 100 is attached to the exhaust duct 12 at a predetermined position between the PDF 14 and the oxidation catalyst 15. Thus, the sensor 100 is responsible for detecting an oxygen concentration and a NOx concentration in the exhaust gas that has passed both the NOx occlusion-reduction type catalyst 13 and the PDF 14.

To the gas concentration sensor 100 is electrically connected a sensor control circuit 200 serving as a "gas concentration calculator." Furthermore, to the sensor control circuit 200 is electrically connected an engine ECU 300 serving as "control means."

In the present embodiment, for injecting the fuel to the engine 10, the design is made such that a lean combustion control is carried out. To realize this control, the engine ECU 300 examines a NOx concentration output coming from the sensor control circuit 200 to perform an air-fuel-ratio feedback control in a lean region in an air-fuel ratio characteristic in addition to other controls, such as the discharge of absorbed and stored NOx and sulfur-poisoning regeneration in the NOx occlusion-reduction type catalyst 13.

Figure 4:
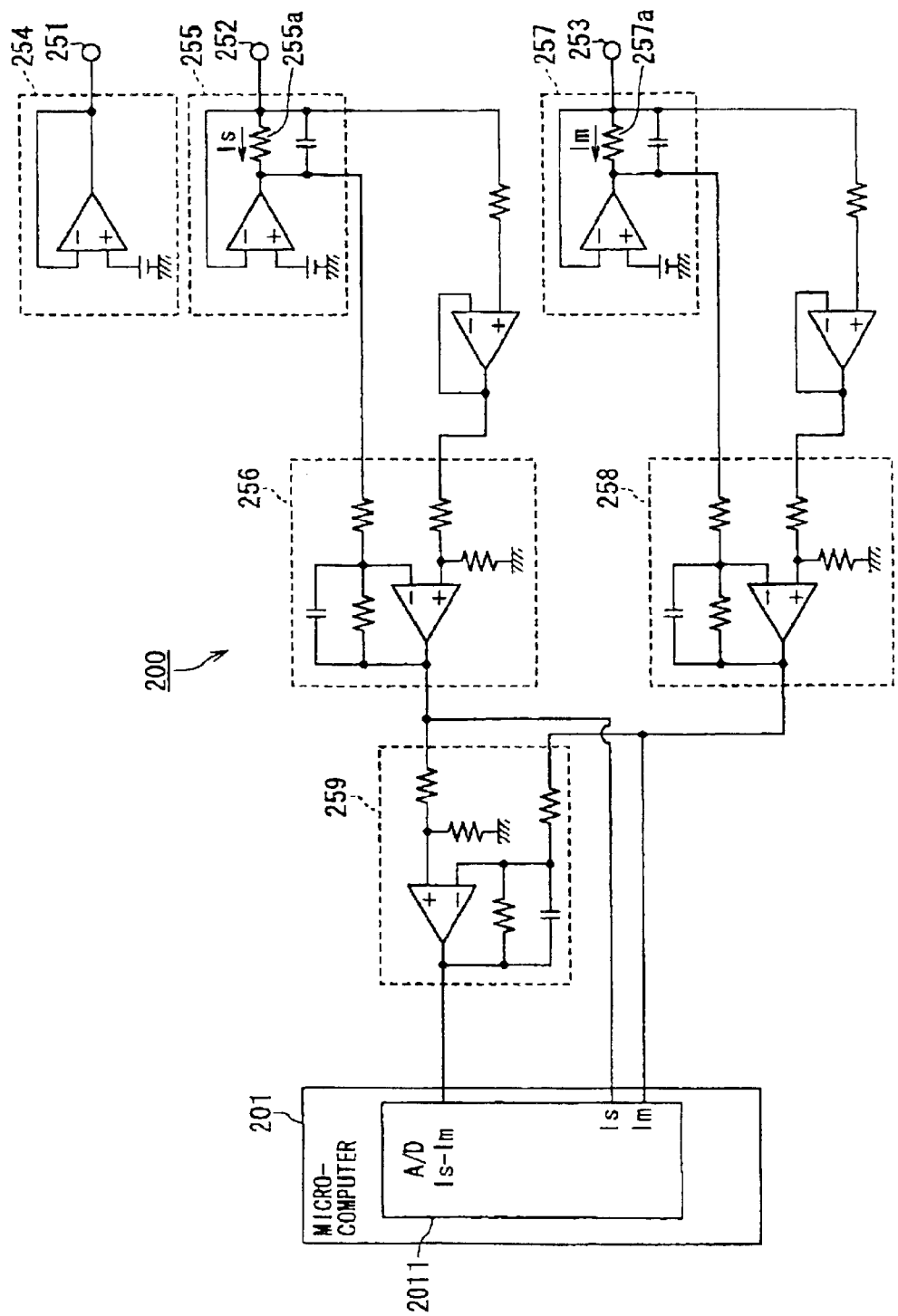
FIG. 4 is a circuit diagram showing the electrical configuration of a sensor control circuit for the gas concentration sensor.

With reference to FIG. 4, the electrical configuration of the sensor control circuit 200 will now be described.

The sensor control circuit 200 is usually equipped with voltage application circuits and current detection circuits for each of the pump cell 110, monitor cell 120 and the sensor cell 130. However, in FIG. 4, for the sake of a simplified explanation, the circuitry for the pump cell 110 is omitted from being depicted, so that only the primary circuit configurations for both the monitor cell 120 and the sensor cell 130 are left.

As shown in FIG. 4, the sensor control circuit 200 is provided with a known microcomputer 201 including a CPU, A/D converters (in the drawing, explained by a representative reference numeral 2011), D/A converters, and I/O ports. The components other than the A/D converters 2011, namely, the CPU, D/A converters, and I/O ports are not shown in the figure. The sensor control circuit 200 has a common electrode terminal 251 electrically connected to the common electrode 122 of both the monitor cell 120 and the sensor cell 130; a sensor cell electrode terminal 252 electrically connected to the electrode 131 of the sensor cell 130; and a monitor cell electrode terminal 253 electrically connected to the electrode 121 of the monitor cell 120.

Of the above terminals 251 to 253, the common electrode terminal 251 is electrically connected to a driver circuit 254 for the common electrode 122. The sensor cell electrode terminal 252 is electrically connected to a driver circuit 255 for the sensor cell electrode. The driver circuit 255 is placed to detect the sensor cell current Is using a current detection resistor 255a. That is, potentials at both ends of the current detection terminal 252a are detected and inputted to a differential amplifying circuit 256. This circuit 256 has a predetermined gain to amplify a difference between the potentials at both ends of the current detection resistor 255a (the potential difference corresponds to a certain amount of censor cell current Is). The amplified sensor cell current Is is outputted to the next circuits.

Electrically connected to the monitor cell electrode terminal 253 is a driver circuit 257 for the monitor cell electrode. The driver circuit 257 is placed to detect the monitor cell current Im using a further current detection resistor 257a. That is, potentials at both ends of the current detection terminal 257a are detected and fed to a differential amplifying circuit 258. This circuit 258 has a predetermined gain to amplify a difference between the potentials at both ends of the current detection resistor 257a (this potential difference corresponds to a certain amount of monitor cell current Im). The amplified monitor cell current Im is outputted to the next circuits.

The outputs of both the differential amplifying circuits 256 and 258 are supplied to not only A/D converters 2011 of the microcomputer 201 but also a further differential amplifying circuit 259. This differential amplifying circuit 259 amplifies, using a predetermined gain, a difference between the outputs of both differential amplifying circuits 256 and 258, and the amplified difference is also supplied as an output signal to one of the A/D converters 2011 of the microcomputer 201. By way of example, the gain at each of the differential amplifying circuits 256 and 258 is set to nearly 1.3 times, while the gain at the final-stage differential amplifying circuit 259 is set to about 4 times.

Figure 5:
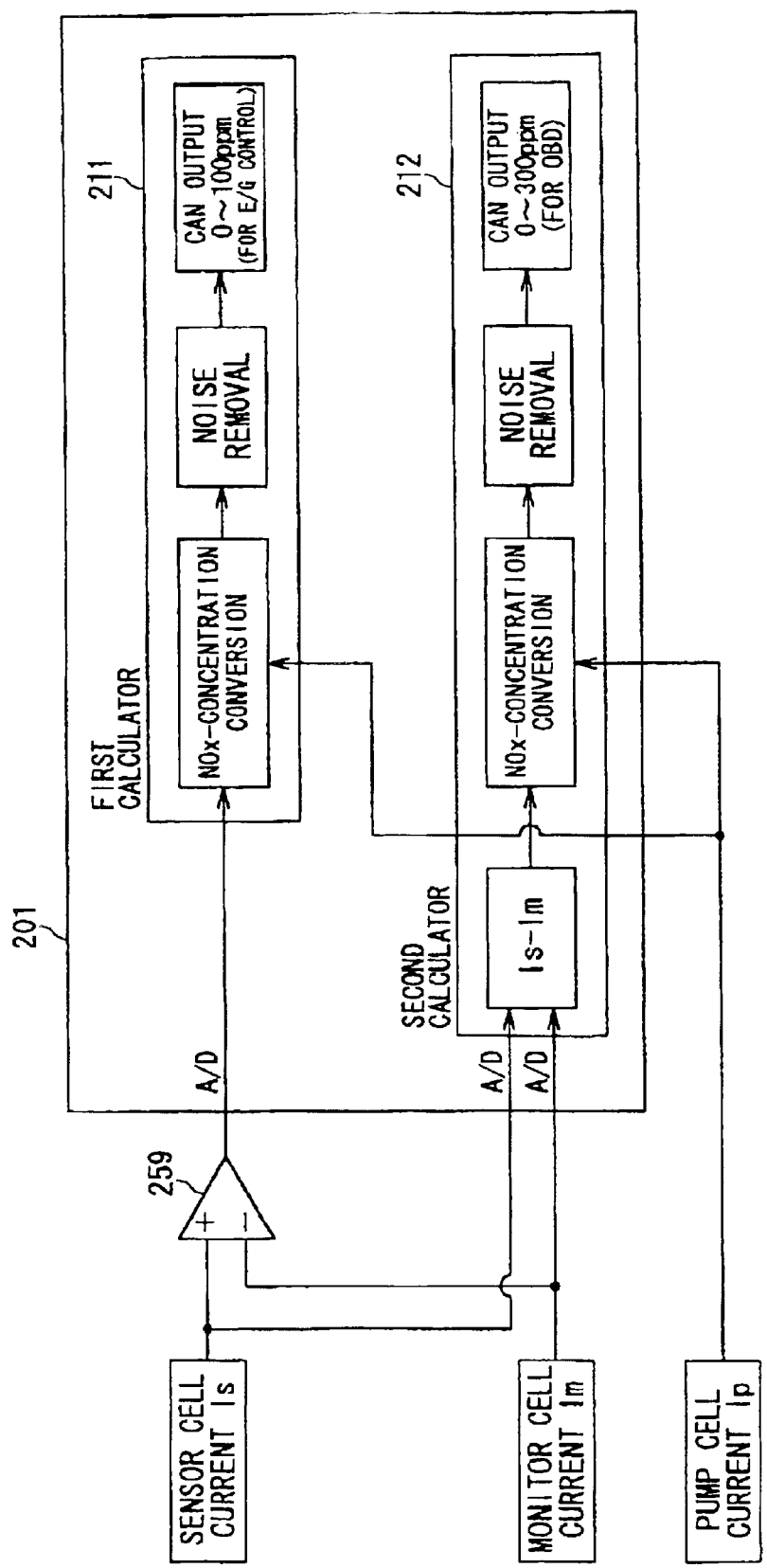
FIG. 5 is a functional diagram carried out a microcomputer incorporated in the sensor control circuit.

FIG. 5 shows the functional configuration of the microcomputer 201 installed in the sensor control circuit 200. In detail, the microcomputer 201 is provided with, in terms of its functions, a first calculator 211 for outputting a NOx concentration given to the engine control and a second calculator 212 for outputting a further NOx concentration given to the OBD. These calculators 211 and 212 serve as concentration calculating means, respectively.

The first and second calculators are configured respectively to calculate NOx concentrations in mutually different detection ranges. The first calculator 211 employs a detection range of 0 to 100 ppm, whilst the second calculator 212 employs a second detection range of 0 to 300 ppm.

The NOx concentration for the engine control can be directed to the following applications. In the exhaust system where, as stated above, the exhaust duct 12 is provided with the NOx occlusion-reduction type catalyst 13, the lean combustion control requires that a large amount of NOx be absorbed by the catalyst 13. Thus a NOx absorption capacity of the catalyst 13 decreases gradually. Hence a decrease in the NOx absorption capacity 13 is detected by monitoring an output signal indicating the NOx concentration, and if needed, a rich spike for NOx deoxidization is performed to discharge the absorbed NOx from the catalyst. Another application is sulfur included in the fuel. Hence the NOx absorption capacity 13 is little by little subjected to sulfur poisoning. It is therefore possible to determine a degree of the sulfur poisoning by monitoring an output signal indicating the NOx concentration, and when needed, a weak rich gas is injected to perform its reproduction. Another application is to determine a deterioration level of the gas concentration sensor 100 by monitoring an output signal indicating the NOx concentration.

Under the OBD regulations, a NOx concentration is detected in a wide detection range extended more than that used for the normal control. In other words, an output signal of the engine-control NOx concentration is detected in a range of 0 to 100 ppm, whereas an output signal of the OBD NOx concentration is detected in a range of 0 to 300 ppm.

The first calculator 211 is configured to read a digitized value of the NOx-detecting current "Is–Im," which is a result calculated by the differential amplifying circuit 259. Using the read digitized value, the first calculator 211 is formed to consecutively carry out NOx-concentration conversion processing, noise removal processing, and CAN output processing. Meanwhile, the second calculator 212 is configured to read digitized values of both the sensor cell current Is and the monitor cell current Im, i.e., the outputs of the differential amplifying circuits 256 and 258, and then consecutively carries out "Is–Im" subtraction processing, NOx-concentration conversion processing, noise removal processing, and CAN output processing using the received digitized values.

To the second calculator 212, both the sensor cell current Is and the monitor cell current Im are given respectively via the different A/D converters 2011, and then the currents Is and Im undergo the subtraction of "Is–Im." As stated before, the sensor cell current Is includes an offset error component, this error component becoming as large as being not negligible (for example, up to approximately 100 nA). A physical maximum value of the A/D converter (one of the A/D converters 2011) detecting the sensor cell current Is should be over the entire NOx-concentration detecting range necessary for the system and the offset error component.

Thus, if the second calculator 211 has a NOx-concentration detection range of 0 to 300 ppm and a maximum sensor cell current of 1200 nA, adding a margin to an offset component 1000 nA requires that the A/D converter has a full scale of 2600 nA. In this condition, a general-purpose 10-bit A/D converter provides a resolution of 2.5 nA/LSB (=2600 nA/1024). This resolution level corresponds to about 1 ppm/LSB, if converted to the NOx concentration.

On the other hand, the first calculator 211 receives the output of the differential amplifying circuit 259 (i.e., the NOx-detecting current "Is–Im") through one of the A/D converters 2011. In this case, no offset error component is included in the NOx-detecting current "Is–Im," because the offset error component has already been cancelled out. Hence it is sufficient if a physical maximum of the dynamic range of the A/D converter, that is, a maximum of the NOx-detecting current satisfies a NOx-concentration detection range necessary for the system.

Hence, in cases where the first calculator 211 is formed to have a NOx-concentration detection range of 0 to 100 ppm and a NOx-detecting current having a maximum 400 nA, the full scale of the A/D converter becomes 600 nA if considering addition of a margin. This leads to a resolution of 0.59 nA/LSB (=600 nA/1024). This shows that the resolution of the first calculator 211 is about four times larger than that of the second calculator 212, thus corresponding to nearly 0.2 ppm/LSB, if converted to the NOx concentration.

In recent years, improvement in the combustion of the engine itself and a reduction in the amount of NOx to be exhausted have been advanced. Under these circumstances, the engine control requires the concentration of NOx to be detected at a precision of about a few ppm. The first calculator 211 is able to sufficiently meet such a strict requirement.

The NOx-concentration conversion, which is carried out by each of the calculators 211 and 212, involves the processing for a NOx-concentration correction. This correction is performed with the use of correction data previously stored in a memory (for instance, a flash ROM) of the microcomputer 201. This correction resolves fluctuations in the sensitivity of the gas concentration sensor 100 and differences among the individual sensors. The corrected NOx concentrations are then subjected to noise removal processing, such as moving average or rounding, to remove noise from the signal indicative of the concentrations. The noise-removed signal is then supplied to the engine ECU 300 with the help of the CAN communication and the D/A converters.

To be specific, the NOx-concentration correction includes such correction items as "correction of zero-point shifts," "correction of sensor cell sensitivity," and "correction of oxygen concentration dependency." These correction items will be explained below. Since each of these correction items differs sensor by sensor in their correction levels to be desired, it is therefore necessary to remove variations among the individual sensors as well. The performance of each of the above correction items is directed to the NOx-detecting current "Is–Im."

(Correction of Zero-Point Shifts)

Figure 6:
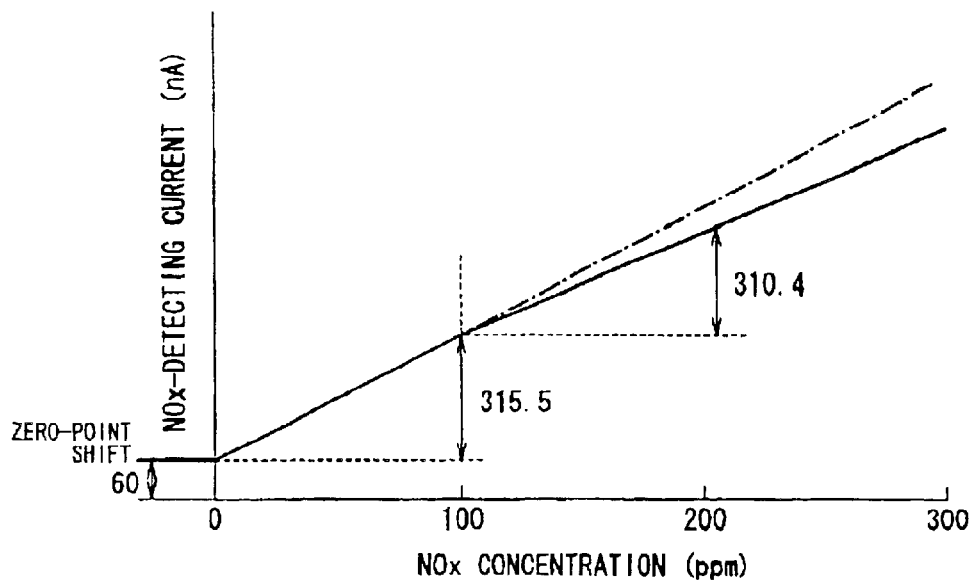
FIG. 6 is a graph explaining characteristics of a NOx detection current obtained when a NOx concentration is changed, the graph showing a zero-point shift.

Under the condition that a NOx concentration is 0 ppm in an ambient atmosphere whose oxygen concentration is 0%, a NOx-detecting current should be zero fundamentally, but does not become zero from a practical standpoint. For instance, as illustrated by the case in FIG. 6, a zero point shifts (in the case shown in FIG. 6, the zero point shifts by 60 nA). An amount of 60 nA correspond to, if converted, to a NOx concentration of 20 ppm or thereabouts, thus causing a non-negligible zero-point shift. Therefore, in the present embodiment, a value for correcting the zero-point shift is determined so that the problem of the zero-point shift can be removed.

(Correction of Sensor Cell Sensitivity)

The detection sensitivity of the sensor cell 130 decreases to some extent with an increase in the NOx concentration. For example, when making a comparison between a lower-concentration range of NOx (0 to 100 ppm) and a higher-concentration range of NOx (100 to 300 ppm) in the case shown in FIG. 6, the former range has a lager inclination than the latter one, showing that the former range is more sensitive to measurement of the NOx-detecting current. The reason is that as the NOx concentration increases, the activity capacity of the sensor cell electrode (NOx-active electrode) comes short, so that sensor cell current decreases. For example, the sensitivity changes slightly at a NOx concentration of 100 ppm (a change of the inclination shown in FIG. 6). If exemplified practically in FIG. 6, a change in the NOx-detecting current occurring corresponding to a concentration change of 100 ppm (0 to 100 ppm) in the lower-concentration range is 315.5 nA, whereas a change in the NOx-detecting current occurring corresponding to a concentration change of 100 ppm (100 to 200 ppm) in the higher-concentration range is 310.4 nA. As understood from these practical figures, there is caused a difference of sensitivity of 1 to 2 ppm or thereabouts between the lower-concentration and higher-concentration ranges.

Thus, the whole detection range of the NOx concentration is divided into plural ranges, and a sensitivity correction coefficient is given range by range. In the present embodiment, to each of a lower-concentration range of 0 to 100 ppm and a higher-concentration range of 100 to 300 ppm, a sensitivity correction coefficient is given. This correction aims at absorption of a sensitively shift occurring in the higher-concentration range.

(Correction of Oxygen Concentration Dependency)

Figure 7:
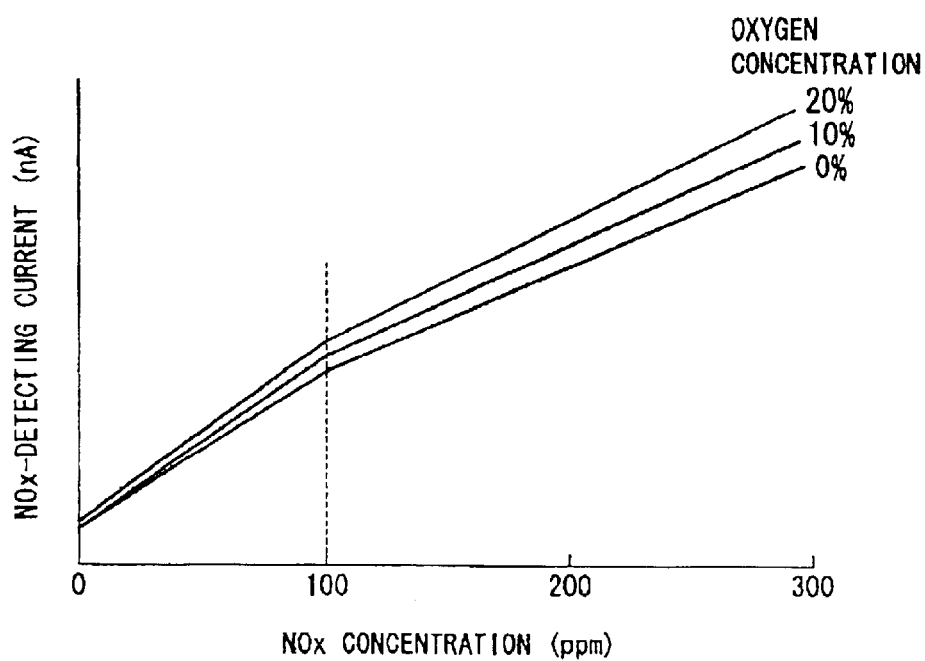
FIG. 7 is another graph explaining characteristics of a NOx detection current obtained when a NOx concentration is changed, in which an oxygen concentration is taken as a parameter.

As shown in FIG. 7, the NOx-detecting current fluctuates depending on an oxygen concentration in an exhaust gas, even if the concentration of the NOx is the same. Specifically, there is a tendency that higher the oxygen concentration, the larger the fluctuations. This results from the following reason. In the pump cell 110, the oxygen, which is an obstacle to the detection of the NOx, is discharged from the first chamber 144, but an exhaust gas having a certain amount corresponding to an amount of the discharged oxygen is newly introduced into the first chamber 144. This extra introduction of the exhaust gas increases the amount of the NOx, which results in that the higher the oxygen concentration in the exhaust gas, the larger the NOx-detecting current (i.e., the censor cell current). FIG. 7 shows that differences in the oxygen concentration are reflected in both of differences in numerical values of shifts of the zero point and differences in inclinations of the NOx-detecting current.

In the present embodiment, correcting data, such as data indicative of correcting values for the zero shift and correcting coefficients for the sensitivity, are prepared in dependence upon different levels of the oxygen concentration. Appropriate correcting data to the current oxygen concentration is thus used to correct the concentration of the oxygen. By way of example, the correcting data is mapped in a memory to retain thereof.

The procedures for setting the foregoing correcting data will now be explained.

First, a model gas bench is used to measure the characteristics of a sensor to be targeted. Measuring conditions are for example that the concentration of oxygen is set to 0, 10 and 20%, respectively, and the concentration of a NOx gas is set to 0, 100 and 300 ppm, respectively. Under these conditions, the pump cell current and NOx-detecting current (i.e., the values of sensor cell current and monitor cell current) are measured. FIG. 8A shows measured results of the pump cell current when the concentration of oxygen is 0, 10 and 20%, while FIG. 8B shows measured results of the NOx-detecting current under the condition of the NOx concentration is 0, 100 and 300 ppm each associated with the oxygen concentrations of 0, 10 and 20%.

The foregoing measured results are used to calculate correcting data. FIG. 8C shows practical values obtained when the oxygen concentration is 0, 10 and 20%. This correction data will now be explained by taking the oxygen concentration of 0% as an example.

In the case that the oxygen concentration is 0%, the NOx-detecting current shows 60 nA when the NOx concentration is set to 0 ppm, whereby the value (60 nA) of the NOx-detecting current is employed as a correcting value for zero-point shifts. In addition, when the detection range of the NOx concentration is divided into two ranges consisting of the lower and higher ranges, as described before, a point at which the ranges are switched becomes a value of the NOx-detecting current obtained when the NOx concentration is 100 ppm. Thus, a NOx-detecting current of 375.46 nA is employed as a range-determining value. For each of the lower and higher ranges, a sensitivity-correcting coefficient is thus figured out by a unit of ppm/nA.

Concretely, for the lower concentration range of 0 to 100 ppm, a changed amount of concentration over this range (i.e., 100 ppm) is divided by a changed amount of NOx-detecting currents (i.e., a current amount of "375.46 nA–60 nA"), thus providing a sensitivity-correcting coefficient= 0.317 [ppm/nA]. Like this, for the higher concentration range of 100 to 300 ppm, a changed amount of concentration over this higher range (i.e., 200 ppm) is divided by a changed amount of NOx-detecting currents (i.e., a current amount of "996.58 nA–375.46 nA"), thus providing another sensitivity-correcting coefficient=0.322 [ppm/nA]. In the similar way to the above, correcting data necessary when the oxygen concentration is 10% and 20% can be calculated, respectively.

As described above, the correcting data is written into memories such as flash ROMs in the memory manufactures' factories before shipping the memories. The memories can be shipped with identification codes, such as bar codes or QR codes (i.e., two-dimensional codes). In such a case (that is, the identification codes are used), it is not always necessary to ship the gas concentration sensors and their control circuits in a one-to-one combination. Based on the identification codes, a vehicle manufacturer is able to write the correcting data by their own, thus reducing the processes necessary for logistics and management sections.

Though the above explanation is given to the case where the detection range of the NOx concentration is sectioned into the two ranges consisting of the lower and higher ranges each of which has its own sensitivity-correcting coefficient, this is not a definitive list. The detection range of the NOx concentration can be divided into three or more ranges. For instance, the detection range can be divided into three ranges of 0 to 100 ppm, 100 to 200 ppm, and 200 to 300 ppm according to the concentration. In such a case, each of the divided three ranges is allowed to have its own sensitivity-correcting coefficient and numerical values of the NOx-detecting current collected at each of NOx concentrations= 100 and 200 ppm can be employed as the range-determining values. As the number of divided ranges increases, accuracy in correcting the concentration can be made higher, thus improving the precision of detecting the NOx concentration.

Figure 9:
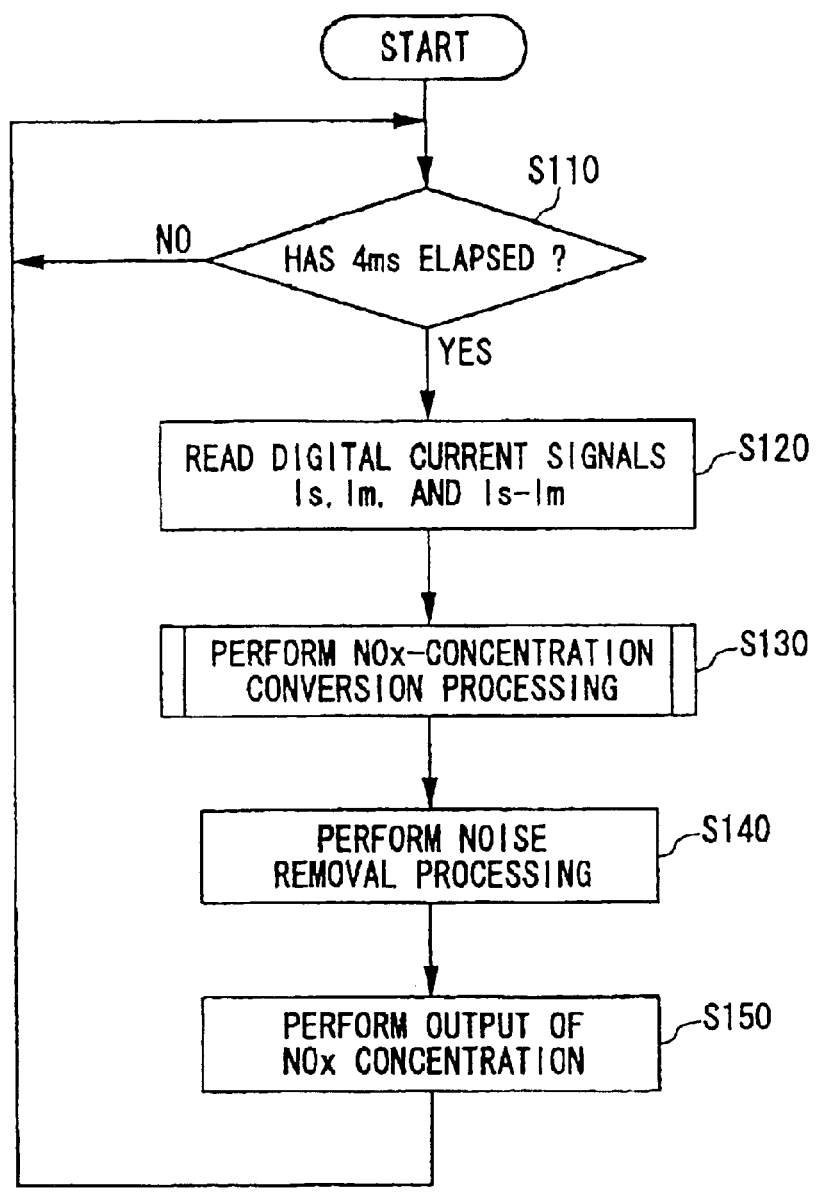
FIG. 9 is a flowchart showing the procedures for supplying the NOx concentration.

With reference to FIG. 9, the processes for outputting the NOx concentration, which is carried out by the microcomputer 201, will now be explained.

In FIG. 9, at step S110, it is determined whether or not a predetermined period of time (in the present embodiment, 4 ms, for instance) has elapsed from the last detection of an A/F (oxygen concentration) and a NOx concentration. This predetermined period of time equals a period of detection of the NOx concentration. When the determination at step S110 is YES, the processing is made to proceed to step S120, where current signals from the gas concentration sensor 100 are taken into the microcomputer 201 through the A/D converters 2011. The taken-in digital current signals include a sensor cell current Is, monitor cell current Im, and NOx-detecting current "Is–Im." The digitized sensor cell current Is and the monitor cell current Im are, after taking them in, subjected to the calculation of "Is–Im."

Then, at step S130, the NOx-detecting current is converted to a corresponding NOx concentration (that is, NOx-concentration conversion processing is carried out). This conversion involves a NOx-concentration conversion that uses the foregoing correcting data. The processing is then made to go to step S140, where the converted NOx concentration undergoes noise removal processing based on moving average or rounding. At step S150, the CAN communication and A/D converters 2011 are utilized to output the NOx concentration.

Figure 10:
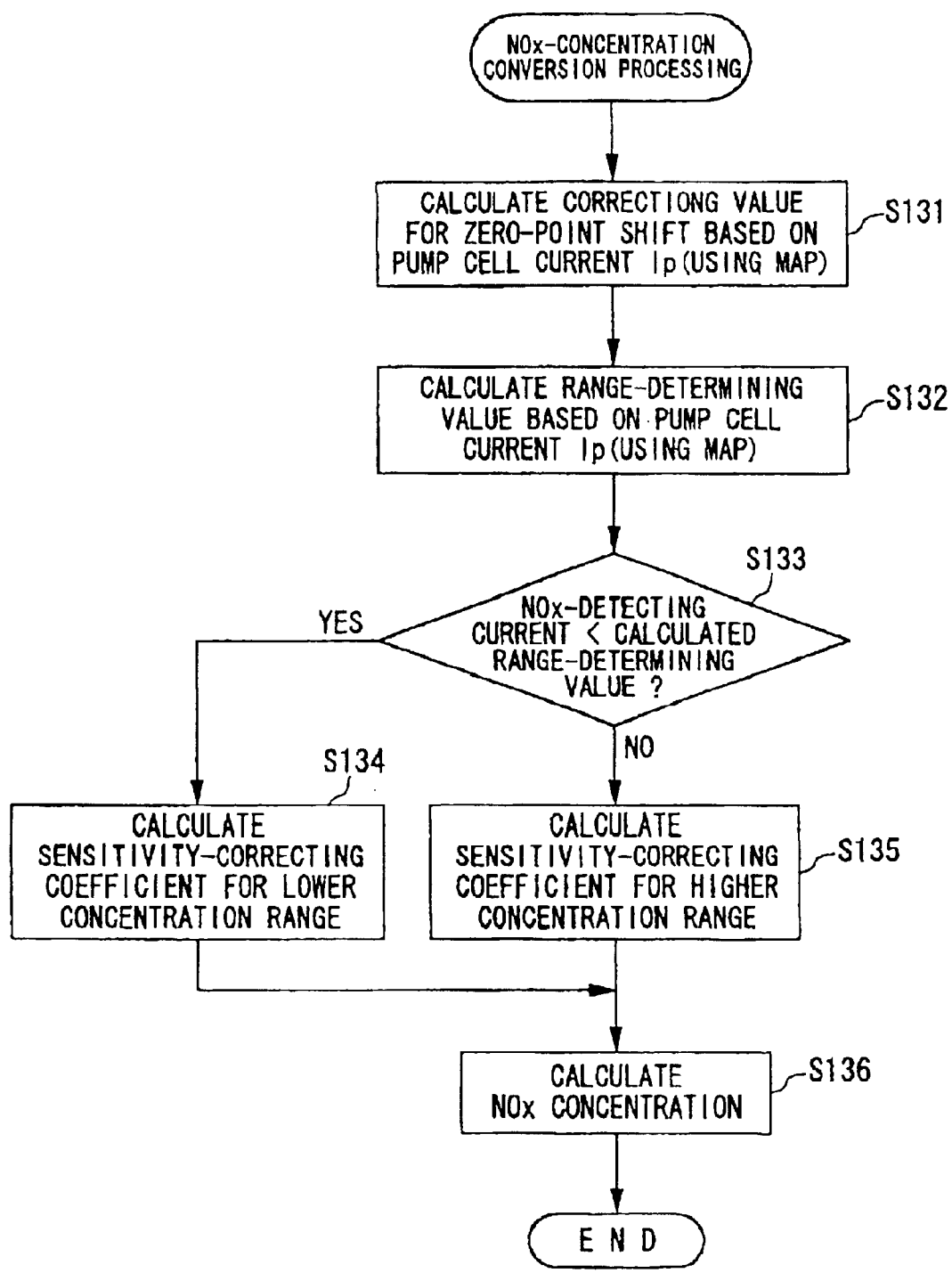
FIG. 10 is a flowchart showing the processing for converting the NOx concentration.

The foregoing NOx-concentration conversion processing at step S130 will now be detailed in connection with FIG. 10.

At step S131, based on the current pump cell current Ip, a correcting value for the zero-point shift of the NOx-detecting current (Is–Im) is calculated with the use of a map. In the data in the map, the correcting data shown in FIG. 8C is reflected. Such map data is used to calculate the correcting value for the zero-point shift. For example, if the pump cell current Ip is 1.25 mA, the zero-point shift correcting value is calculated as being 63 nA. At step S132, the range-determining value is then calculated with a map on the basis of the pump cell current Ip. Like the foregoing, if the pump cell current Ip=1.25 mA, a range-determining value of 406.6 nA is calculated.

Then, at step S133, it is determined if the current NOx-detecting current is smaller than the calculated range-determining value or not. If the determination reveals that the NOx-detecting current is smaller than the calculated range-determining value, the processing goes to step S134, at which the sensitivity-correcting coefficient for the lower concentration range (a range of 0 to 100 ppm) is calculated with the use of a map. On the other hand, if the determination reveals that the NOx-detecting current is equal to or larger than the calculated range-determining value, the processing goes to step S135, where the sensitivity-correcting coefficient for the higher concentration range (a range from 100 to 300 ppm) is calculated by using a map. If assuming that, as exemplified as before, the pump cell current Ip=1.25 mA, the sensitivity-correcting coefficient for the lower concentration range is 0.291 [ppm/nA], for example.

Finally, at step S136, the above calculated correcting data are used to calculate a NOx concentration from the current NOx-detecting current. To be specific, if the NOx-detecting current is 372.3 nA, the above zero-point shift correcting value (63 nA) and the sensitivity-correcting coefficient (0.291 [ppm/nA]) are introduced into calculation as follows.

$$\text{NOx concentration [ppm]} = (372.3 - 63)0.291 = 90.0$$

Thus, a NOx concentration of 90.0 is resulted from the calculation.

The present embodiment, which has been described so far, provides the following various advantages.

The microcomputer 201 has functionally the two calculators (the first calculator 211 and the second calculator 212) and different (lower and higher) concentration-detecting ranges are set to the calculators 211 and 212, respectively. This allows both the calculators 211 and 212 to be given resolution of NOx concentrations, respectively, with the result that a desired precision for detecting a gas concentration can be obtained in any application. In particular, in the present embodiment, the first calculator 211 is able to dedicate its calculation capacity to a high-accuracy NOx concentration for use in engine control, whereas the second calculator 212 does to a NOx concentration in a wider range for use in failure diagnosis.

Further, the sensor control circuit 200 has the configuration that an offset error component (i.e., a component given by a monitor cell current) contained in the sensor cell current is removed by the differential amplifier 259. It is therefore possible that the gain at the differential amplifier 259 can be made larger, whereby the dynamic range of the A/D converter (i.e, one of the A/D converters 2011) can be set to a larger value. The resolution at the A/D converter can be raised depending on an increase in the gain. Particularly, such a configuration for obtaining the enhanced resolution is arranged to the circuitry leading to the first calculator 211, thus ensuring an improvement in the precision for detecting the NOx concentration.

Still, the NOx-concentration conversion involves the performance of the correction of zero-point shifts, correction of sensor cell sensitivity, and correction of oxygen-concentration dependency. Hence the actual characteristics of each gas concentration sensor are surely reflected into the NOx-concentration conversion. It is therefore possible to further improve the precision for detecting a NOx concentration. The above various types of correction can be individualized sensor by sensor, so that individual differences among gas concentration sensors are eliminated.

A variety of types of modifications according to the present invention can still be reduced into practice as follows.

A first modification concerns with the location of the differential amplifier. The circuitry shown in FIG. 5 has the differential amplifier 259 placed before the A/D converter in the line connected to the first calculator 211 so that the NOx-detecting current "Is–Im" can be detected by the differential amplifier 259. Alternatively, the differential amplifier may be placed before the A/D converter in the line connected to the second calculator 212 in order to detect the NOx-detecting current "Is–Im." Another alternative is that the first calculator is configured to directly receive, as input signals to be A/D-converted, both the sensor cell current Is and the monitor cell current Im without the mutual subtraction (that is, without the calculation of a NOx-detecting current which is carried out by the differential amplifier).

A second modification is concerned with the number of calculators. The foregoing embodiment adopts the two calculators (i.e., the first and second calculators) realized functionally by the microcomputer 201, but this is not definitive. Three or more calculators may be placed.

A third modification is concerned with how to calculate the NOx concentration. In the above embodiment, the NOx concentration has been computed using the NOx-detecting current "Is–Im" obtained by subtracting the monitor cell current Im (corresponding to an offset error component) from the sensor cell current Is. Instead of this, the NOx concentration can be computed from only the sensor cell current (i.e., without using the monitor cell current). The reason is as follows. It is understood that the monitor cell current is consistent with a concentration of the residual oxygen in the chamber. If it can be assumed that the pump cell keeps the concentration of the residual oxygen constant, an offset error current contained in the sensor cell current can be regarded as being constant. Hence, treating the offset error being constant will eliminate the necessity of measuring the monitor cell current.

A fourth modification concerns another structure of the gas concentration sensor. In the foregoing embodiment, the gas concentration sensor has been structured as shown in FIGS. 1A and 1B, but the sensor can be constructed as shown in FIG. 11, instead.

Figure 11:
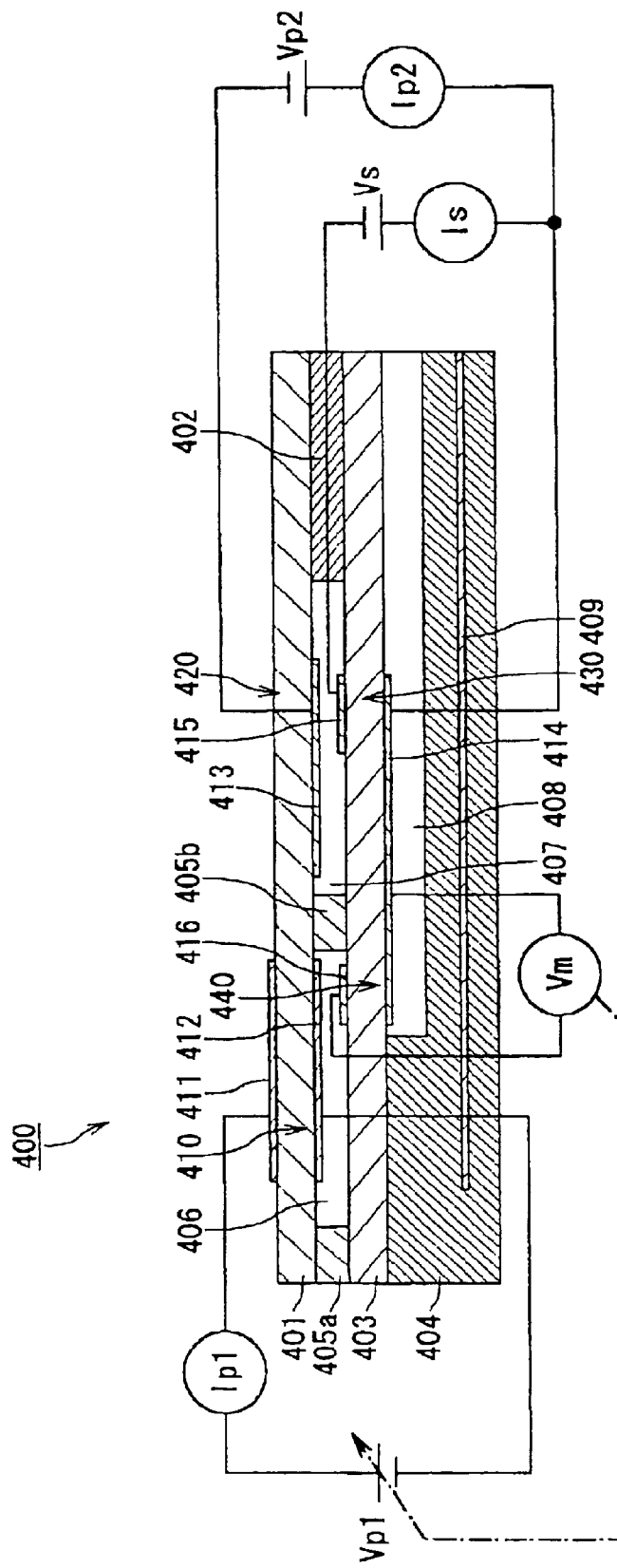
FIG. 11 is a section view showing a modification of the gas concentration sensor according to the embodiment.

The gas concentration sensor 400 shown in FIG. 11 adopts sheet-like members 401 to 404 each of which is made of solid electrolyte (for instance, zirconia) and layered one on another. Between the sheet-like members 401 and 403, a first chamber 406 and a second chamber 407 are formed by partitioning the space with rate-determining layers 405a and 405b. An atmosphere-communicating passage 404 is formed in the sheet-like member 404 jointly with the juxtaposed sheet-like member 403. A heater 409 is embedded in the sheet-like member 404.

Further, this gas concentration sensor 400 has a first pump cell 410, a second pump cell 420, a sensor cell 430, and a monitor cell 440, which are mutually layered with the solid electrolyte layers therebetween, which is a feature of the sensor 400. In this layered structure, the first pump cell 410 has a pair of electrodes 411 and 412 to which a voltage Vp1 is applied, and a first pump cell Ip1 that flows in response to the application is detected. The second pump cell 420 has a pair of electrodes 413 and 414 to which a voltage Vp2 is applied, and a second pump cell Ip2 that flows in response to the application is detected. Similarly, the sensor cell 430 has a pair of electrodes 414 and 415 to which a voltage Vs is applied, and a sensor cell current Is that flows in response to the application is detected. In the monitor cell 440, an electromotive force signal Vm is detected between two electrodes 414 and 416.

An exhaust gas is introduced into the first chamber 406 via the rate-determining layer 405a. Most of the oxygen contained in the exhaust gas is detected through the detection of the electromotive force Vm at the monitor cell 440 and allowed to be discharged via the electrode 411 by controlling the application voltage Vp1 to the first pump cell 410 corresponding to the electromotive force Vm. The remaining gas is introduced into the second chamber 407 through the rate-determining layer 405b, and the residual oxygen in the remaining gas is dissolved at the second pump cell 420 responsively to the application of the voltage Vp2, thus being discharged into the atmosphere-communicating passage 408. A NOx component in the gas is dissolved at the sensor cell 430 responsively to the application of the voltage Vs, thus being discharged into the atmosphere-communicating passage 408. Based on a sensor cell current Is flowing responsively to the application, a NOx concentration value is computed. In the gas concentration sensor 400 shown in FIG. 11, the first pump cell 410, sensor cell 430, and second pump cell 420 correspond to the first sell, second cell and third cell, respectively.

Figure 12:
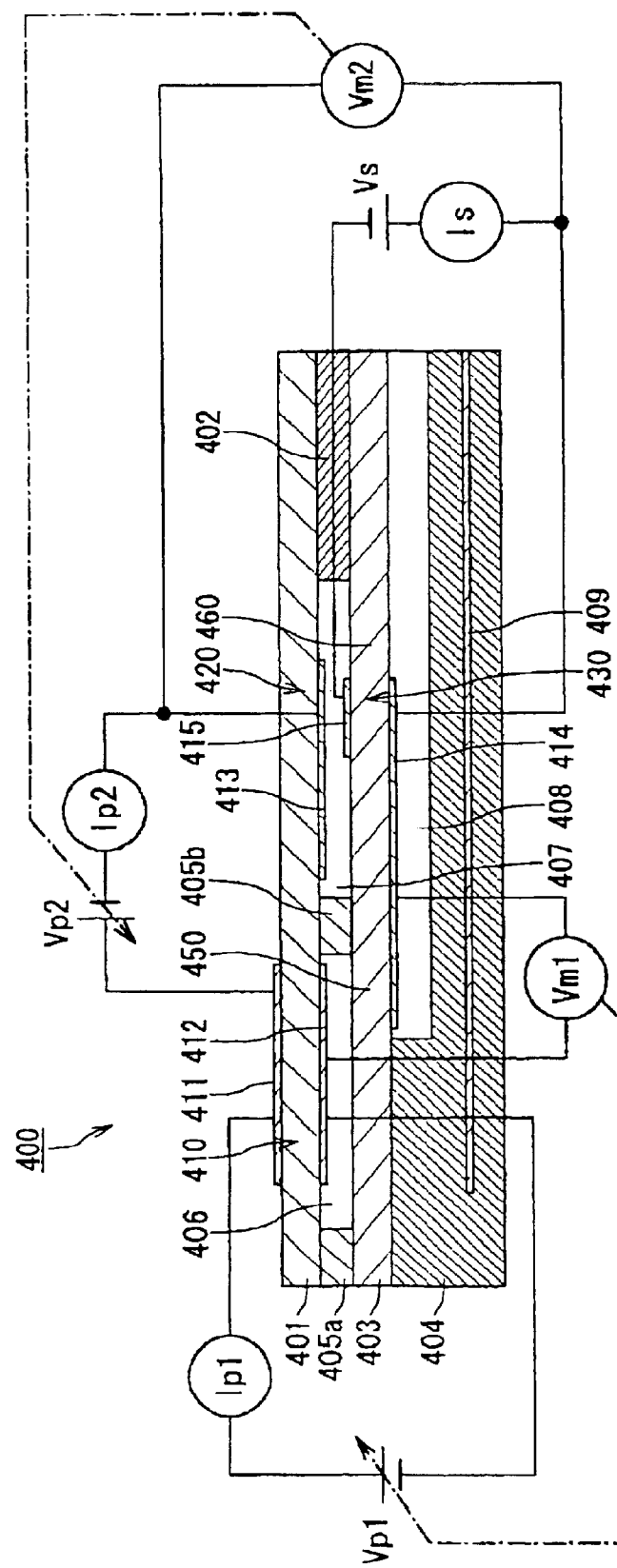
FIG. 12 is a section view showing another modification of the gas concentration sensor according to the embodiment.

Furthermore, a fifth modification concerns another structure of the gas concentration sensor, which is a gas concentration sensor 400 shown in FIG. 12, which is further modified from the structure shown in FIG. 11. This sensor is constructed such that, at the first pump cell 410, a voltage Vp1 is applied to the paired electrodes 411 and 412 and the first pump cell current Ip1 that flows responsively to the application is detected. At the pump cell 420, a voltage Vp2 is applied between both the electrodes 411 and 413, and a second pump cell current Ip2 flowing in response to the application is detected. Further, at the sensor cell 430, a voltage Vs is applied between the electrodes 414 and 415 to detect a sensor cell current Is that flows responsively to the application. Further, at the first monitor cell 450, an electromotive force signal Vm1 is detected between the electrodes 412 and 414, while at the second monitor cell 460, an electromotive force signal Vm2 is detected between the electrodes 413 and 414.

The gas concentration sensor 400 shown in FIG. 12 operates as follows. An exhaust gas is introduced into the first chamber 406 via the rate-determining layer 405a, and then most of the oxygen contained in the exhaust gas is detected through the detection of the electromotive force Vm1 at the first monitor cell 450 and allowed to be discharged via the electrode 411 by controlling the application voltage Vp1 to the first pump cell 410 corresponding to the electromotive force Vm1. The remaining gas is introduced into the second chamber 407 via the rate-determining layer 405b. In the second chamber 407, the residual oxygen in the gas is detected through the detection of the electromotive force signal Vm2 at the second monitor cell 460, and is discharged outside via the electrode 411 by controlling the application voltage Vp2 to the second pump cell 420 in accordance with the signal Vm2. The NOx in the exhaust gas is dissolved by the application of the voltage Vs, before being discharged into the atmosphere-communicating passage 408. The censor cell current Is that flows responsively to the application is used to calculate a concentration of the NOx. In the gas concentration sensor 400 shown in FIG. 12, the first pump cell 410, sensor cell 430, and second pump cell 420 correspond to the first sell, second cell and third cell, respectively.

The gas concentration sensor according to the present invention is not limited to applications for detecting the NOx concentration, but can be applied to detection of concentrations of HO and CO which can be exemplified as specific gas components. In such cases, the pump cell is used to discharge residual oxygen contained in a gas to be detected, and a senor cell is used to dissolve a HC or CO component in a gas from which the residual oxygen has been already discharged, with a concentration of the HC or CO component detected. Furthermore, the gas concentration sensor according to the present invention is also applicable to applications other than for use in automobiles. It is also possible to detect various types of gases other than an exhaust gas by the sensor according to the present invention.

For the sake of completeness, it should be mentioned that the various embodiments and modifications explained so far are not definitive lists of possible embodiments. The expert will appreciates that it is possible to combine the various construction details or to supplement or modify them by measures known from the prior art without departing from the basic inventive principle.

The entire disclosure of Japanese Patent Application No. 2002-297773 filed on Oct. 10, 2002 including the specification, claims, drawings and summary is incorporated herein by reference in its entirety.

What is claimed is:

1. A gas concentration detecting apparatus comprising:
   a gas concentration sensor provided with
      a first cell for discharging oxygen contained in a gas to be detected introduced in a chamber from the chamber and for charging oxygen into the chamber,
      a second cell for detecting a concentration of a specific gas component of the gas that has passed along the first cell, and
      a third cell for detecting a concentration of residual oxygen in the gas that remains after the oxygen has been discharged through the first cell; and
   a gas concentration calculator configured to take in a current signal acquired from the second cell measured with a voltage applied to at least the second cell and calculate the concentration of the specific gas component based on the current signal acquired from the second cell, the gas concentration calculator including a plurality of concentration calculating means of which concentration detecting ranges are different in a scale from each other and the concentration of the specific gas component being calculated every concentration calculating means.

2. The gas concentration detecting apparatus according to claim 1, wherein the gas concentration calculator is provided with a plurality of controllers to which the concentrations of the specific gas component calculated by the concentration calculating means are supplied, respectively.

3. The gas concentration detecting apparatus according to claim 2, wherein the gas concentration sensor is arranged to an exhaust duct of an engine mounted in a vehicle so that an exhaust gas flowing through the exhaust duct is treated as the gas to be detected and a concentration of a specific gas component of the exhaust gas is detected, wherein, of the plurality of concentration calculating means, concentration calculating means of which concentration detecting range is smaller is assigned to calculation of the concentration of the specific gas component for controlling the engine and further concentration calculating means of which concentration detecting range is larger is assigned to calculation of the concentration of the specific gas component for diagnosing a fault of the engine.

4. The gas concentration detecting apparatus according to claim 3, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

5. The gas concentration detecting apparatus according to claim 3, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, both of the differential amplifying circuit and the A/D converter belonging to, of the plurality of concentration calculating means, concentration calculating means of which concentration detecting range is small, whereby the digitized signal is provided to the computation of the concentration of the specific gas component.

6. The gas concentration detecting apparatus according to claim 1, wherein the gas concentration sensor is arranged to an exhaust duct of an engine mounted in a vehicle so that an exhaust gas flowing through the exhaust duct is treated as the gas to be detected and a concentration of a specific gas component of the exhaust gas is detected, wherein, of the plurality of concentration calculating means, concentration calculating means of which concentration detecting range is smaller is assigned to calculation of the concentration of the specific gas component for controlling the engine and further concentration calculating means of which concentration detecting range is larger is assigned to calculation of the concentration of the specific gas component for diagnosing a fault of the engine.

7. The gas concentration detecting apparatus according to claim 1, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

8. The gas concentration detecting apparatus according to claim 1, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, both of the differential amplifying circuit and the A/D converter belonging to, of the plurality of concentration calculating means, concentration calculating means of which concentration detecting range is small, whereby the digitized signal is provided to the computation of the concentration of the specific gas component.

9. The gas concentration detecting apparatus according to claim 1, wherein the gas concentration sensor is arranged to an exhaust duct of an engine mounted in a vehicle so that an exhaust gas flowing through the exhaust duct is treated as the gas to be detected and a concentration of a specific gas component of the exhaust gas is detected, wherein, of the plurality of concentration calculating means, concentration calculating means of which concentration detecting range is smaller is assigned to calculation of the concentration of the specific gas component for controlling the engine and further concentration calculating means of which concentration detecting range is larger is assigned to calculation of the concentration of the specific gas component for diagnosing a fault of the engine.

10. The gas concentration detecting apparatus according to claim 9, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

11. The gas concentration detecting apparatus according to claim 9, wherein the gas concentration sensor is further provided with a circuit configured to measure a current signal acquired from the third cell measured with a voltage applied to the third cell and the gas concentration calculator is further provided with a differential amplifying circuit to receive both the current signals coming from the second and third cells and differentially amplify both the current signals and a A/D converter to digitize a result signal outputted from the differential amplifying circuit, both of the differential amplifying circuit and the A/D converter belonging to, of the plurality of concentration calculating means, concentration calculating means of which concentration detecting range is small, whereby the digitized signal is provided to the computation of the concentration of the specific gas component.

12. The gas concentration detecting apparatus according to claim 1, wherein the gas concentration calculator is provided with means for correcting sensitivity in computing the concentration of the specific gas component depending on the current concentration of the specific gas component.

13. The gas concentration detecting apparatus according to claim 1, wherein the gas concentration calculator is provided with means for correcting an oxygen concentration dependency in computing the concentration of the specific gas component depending on a current concentration of oxygen included in the gas to be detected.

14. The gas concentration detecting apparatus according to claim 1, wherein the gas concentration calculator is provided with a memory in which map data is stored, the map data being defined by employing as parameters both of the concentration of the specific gas component included in the gas to be detected and a concentration of oxygen included in gas to be detected, means for setting a sensitivity correction coefficient by using the map data depending on the current concentrations of the specific gas component and the oxygen, and means for correcting the concentration of the specific gas component with the use of the sensitivity correction coefficient.

15. A gas concentration detecting apparatus comprising:
a gas concentration sensor provided with
    a first cell for discharging oxygen contained in a gas to be detected introduced in a chamber from the chamber and for charging oxygen into the chamber,
    a second cell for detecting a concentration of a specific gas component a gas that has passed along the first cell, and
    a third cell for detecting a concentration of residual oxygen in the gas that remains after the oxygen has been discharged through the first cell; and
a gas concentration calculator is provided with a circuit to take in a current signal acquired from the second cell measured with a voltage applied to the second cell and to take in a current signal acquired from the third cell measured with a voltage applied to the third cell, a differential amplifying circuit to receive both the current signals coming from the second and third cells and differentially amplify both the current signals and a A/D converter to digitize a result signal outputted from the differential amplifying circuit, whereby the digitized signal is provided to the computation of the concentration of the specific gas component.

16. The gas concentration detecting apparatus according to claim 15, wherein the gas concentration calculator is provided with means for correcting sensitivity in computing the concentration of the specific gas component depending on the current concentration of the specific gas component.

17. The gas concentration detecting apparatus according to claim 16, wherein the gas concentration calculator is provided with means for correcting an oxygen concentration dependency in computing the concentration of the specific gas component depending on a current concentration of oxygen included in the gas to be detected.

18. The gas concentration detecting apparatus according to claim 17, wherein the gas concentration calculator is provided with a memory in which map data is stored, the map data being defined by employing as parameters both of the concentration of the specific gas component included in the gas to be detected and a concentration of oxygen included in gas to be detected, means for setting a sensitivity correction coefficient by using the map data depending on the current concentrations of the specific gas component and the oxygen, and means for correcting the concentration of the specific gas component with the use of the sensitivity correction coefficient.

19. The gas concentration detecting apparatus according to claim 15, wherein the gas concentration calculator is provided with means for correcting an oxygen concentration dependency in computing the concentration of the specific gas component depending on a current concentration of oxygen included in the gas to be detected.

20. The gas concentration detecting apparatus according to claim 15, wherein the gas concentration calculator is provided with a memory in which map data is stored, the map data being defined by employing as parameters both of the concentration of the specific gas component included in the gas to be detected and a concentration of oxygen included in gas to be detected, means for setting a sensitivity correction coefficient by using the map data depending on the current concentrations of the specific gas component and the oxygen, and means for correcting the concentration of the specific gas component with the use of the sensitivity correction coefficient.

\* \* \* \* \*